United States Patent [19]

Atkinson

[11] 4,042,829
[45] Aug. 16, 1977

[54] FREQUENCY DOMAIN DISCRIMINATION AND COUNTING TECHNIQUE

[75] Inventor: E. Ronald Atkinson, Bethesda, Md.

[73] Assignee: The United States of America as represented by the Secretary of the Navy, Washington, D.C.

[21] Appl. No.: 628,706

[22] Filed: Nov. 4, 1975

[51] Int. Cl.² .................... G06M 7/00; G02B 27/38
[52] U.S. Cl. ........................ 250/550; 250/222 PC; 250/570
[58] Field of Search ............ 250/550, 576, 233, 232, 250/236, 214 PC, 222 PC; 356/102, 208, 197; 350/162 SF

[56] References Cited

U.S. PATENT DOCUMENTS

| | | | |
|---|---|---|---|
| 3,364,811 | 1/1968 | Baruch et al. | 250/576 |
| 3,733,136 | 5/1973 | Porath-Furedi | 356/197 |
| 3,743,427 | 7/1973 | Weiser | 356/124 |
| 3,809,478 | 5/1974 | Talbot | 356/102 |
| 3,833,864 | 9/1974 | Kiess et al. | 250/576 |

FOREIGN PATENT DOCUMENTS 1,227,254  10/1966  Germany .............................. 250/576

OTHER PUBLICATIONS

Fallon, "Design Consideration for a Linear Microdensitometer", Optical Engineering, vol. 12, No. 6, p. 206.

Primary Examiner—Alfred E. Smith
Assistant Examiner—David K. Moore
Attorney, Agent, or Firm—R. S. Sciascia; Roy Miller

[57] ABSTRACT

An apparatus and method for counting the number of objects-of-interest present in a selected sample by scanning the sample with a rotating reticle of preselected design to measure the spatial frequency components in the field-of-view, which components are definitive of the number of objects-of-interest present. The spacing within the reticle pattern determines the size of the objects that will be counted. The invention has significant application as a means for counting bone marrow granulocyte precursor colonies in the detection and treatment of leukemia.

11 Claims, 4 Drawing Figures

FREQUENCY DOMAIN DISCRIMINATION AND COUNTING TECHNIQUE

BACKGROUND OF THE INVENTION

The problem of discriminating and counting the number of objects randomly distributed in a visual field is encountered in many technologies. The determination of: size distribution in powders, particulate matter in gasses, events represented by grains in nuclear emulsions, cloud cover in satellite photographs, and bacterial colonies in culture are some examples which are approached by visual counting. A whole class of instruments for systematizing, automating, and reducing the errors of manual counting are commercially available for many applications.

In those situations where object discrimination is simply based on contrast and size, the number of objects in a size range may be simply related to the spatial frequency content of the visual field containing the objects. A discrimination technique based on far-field diffraction pattern analysis, requiring detailed knowledge of the scattering function, is described by W. L. Anderson and R. E. Beissner in "Applied Optics," 10, 1503 (1971), and J. P. Meric, et. al., in "Optical Communication," 10, 266 (1974). Some pattern recognition techniques, using digital image processing, depend upon the spatial frequency signatures of the objects that are to be counted, as discussed by B. C. Partridge, Proc. 16th Annual Technical Meeting of the Society of Photo-Optical Instrumentation Engineers, 4, 207 (1973). A simple method, long used in missle guidance, for measuring image spatial frequencies by means of rotating reticles has been described by G. F. Aroyan in "Proceedings of the IRE," , 47, 1561 (1959).

The present disclosure provides an analysis of rotating reticle spatial frequency selection as it is applied to counting automation. An example of the utility of this technique applied to the difficult problem of monitoring the growth of irregularly shaped granulocyte precursor cell colonies distributed in a turbid semi-solid medium is disclosed.

DESCRIPTION OF A PREFERRED EMBODIMENT

Figure 1:
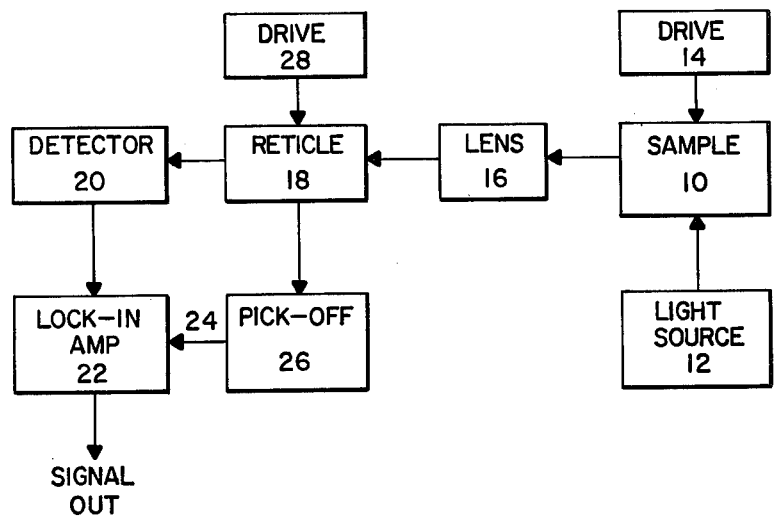
FIG. 1 is a block diagram of an embodiment of the present invention that may be employed to count the number of objects present in a selected sample.

FIG. 1 shows an embodiment of the present invention for counting the number of objects present in a selected sample by automatic measurement of spatial frequency components. Measurements of the spatial frequency components is the measurement of the optical components that together describe the frequency of occurrence of the objects-of-interest by spatial position. Selected sample 10 which includes the objects to be counted, is illuminated by light source 12, and may be rotatably driven by drive 14 to insure that the portion interrogated is a representative volume of the sample. Lens 16 focuses the illumination reflected by sample 10 onto rotating reticle 18 for detection by detector 20. Reticle 18 is driven by drive 28 operates to modulate the information conveyed in the reflected illumination at the reticle's rate of rotation. The output of detector 20 is synchronously detected by lock-in amplifier 22 with reference signal 24 from optical pick-off 26 on the edge of reticle 18. The output provided by amplifier 22 is definitive of the number of objects present in the sample and may be provided in an analog, digital, or other form.

In rotating reticle spatial frequency measurements, a time varying detector signal, $\sigma$, is obtained by passing a spatially periodic reticle pattern, $R$, between a photodetector and the image. If the image is thought of as composed of spatially distributed sources of irradiance $\rho_\kappa$ on the detector, then the detector signal is given by:

$$\sigma(t) = \sum_\kappa \int R(ct-x)\rho(x)dx$$

where $c$ is the reticle velocity along the coordinate of reticle motion, $x$.

In the frequency domain, taking Fourier transforms symbolized by 7

$$7[\sigma(t)] \equiv \sigma(\omega) = \sum_\kappa 7[\int R(et-x)\rho(x)dx]$$

which, by the convolution theorem, may be expressed:

$$\sigma(\omega) = \sum_\kappa 7[R(x)]7[\rho(x)] = \sum_\kappa R(\omega)\rho(\omega).$$

The Fourier transform of the reticle function, $R$, is defined as $$R(\omega) \equiv \frac{1}{\sqrt{2\pi}} \int R(x)\exp(-i\omega x)dx.$$

Since this function is periodic, it may be expressed as a Fourier series summed over discrete frequencies:

$$R(x) = \sum_l r_l \exp(i\omega_l x).$$

Substituting, there results:

$$\sigma(\omega) = \sum_{\kappa, l} r_l \rho(\omega_l)$$

i.e., the periodic reticle has selected discrete spatial frequencies, $\omega_l$, and gives rise to a detector signal which is a weighted average of the spatial frequency amplitudes of objects in the image.

If the image consists of a group of objects identical except for location, i.e., only displaced in phase, then $$\rho_\kappa = \rho \exp(i\delta_\kappa)$$

and the magnitude of the signal for $N$ of these objects becomes:

$$|\sigma|^2 = |\sum_l r_l \rho(\omega_l)|^2 [N + \sum_{m,n}^n \cos(\delta m - \delta n)]$$

Assuming the objects to be randomly distributed relative to each other, the cosine term approaches zero and the signal magnitude is given by $$\sigma = \Sigma_l \, n \, p(\omega_l) \sqrt{N}$$

which is seen to vary with the square root of the number of objects. It is in this property, expressed in the equation immediately above, which permits the number of objects to be determined from the measurement of a detector signal in the frequency domain by means of a rotating reticle.

If the image consists of a superposition of different classes ($j$) of objects numbering $N_j$ each, then the same analysis which led to the final equation above, leads to:

$$|\sigma| = \text{sqrt} \, [\Sigma \alpha_j(\omega_l) N_j]$$

where the coefficients $\alpha_j$ are quantities proportional to the product of the square of the spatial frequency amplitude of the objects in the class and the square of the reticle spatial frequency. A given reticle spacing will, therefore, select objects in a given size range, i.e., those having a large spatial frequency component at the reticle spacing, and produce a signal amplitude at the reticle frequency of rotation which is proportional to the square root of the number of objects in this size range. The frequency response of a "square wave" reticle to Gaussian shaped objects as a function of ratio of object size to reticle spacing is given in FIG. 2.

Figure 4:
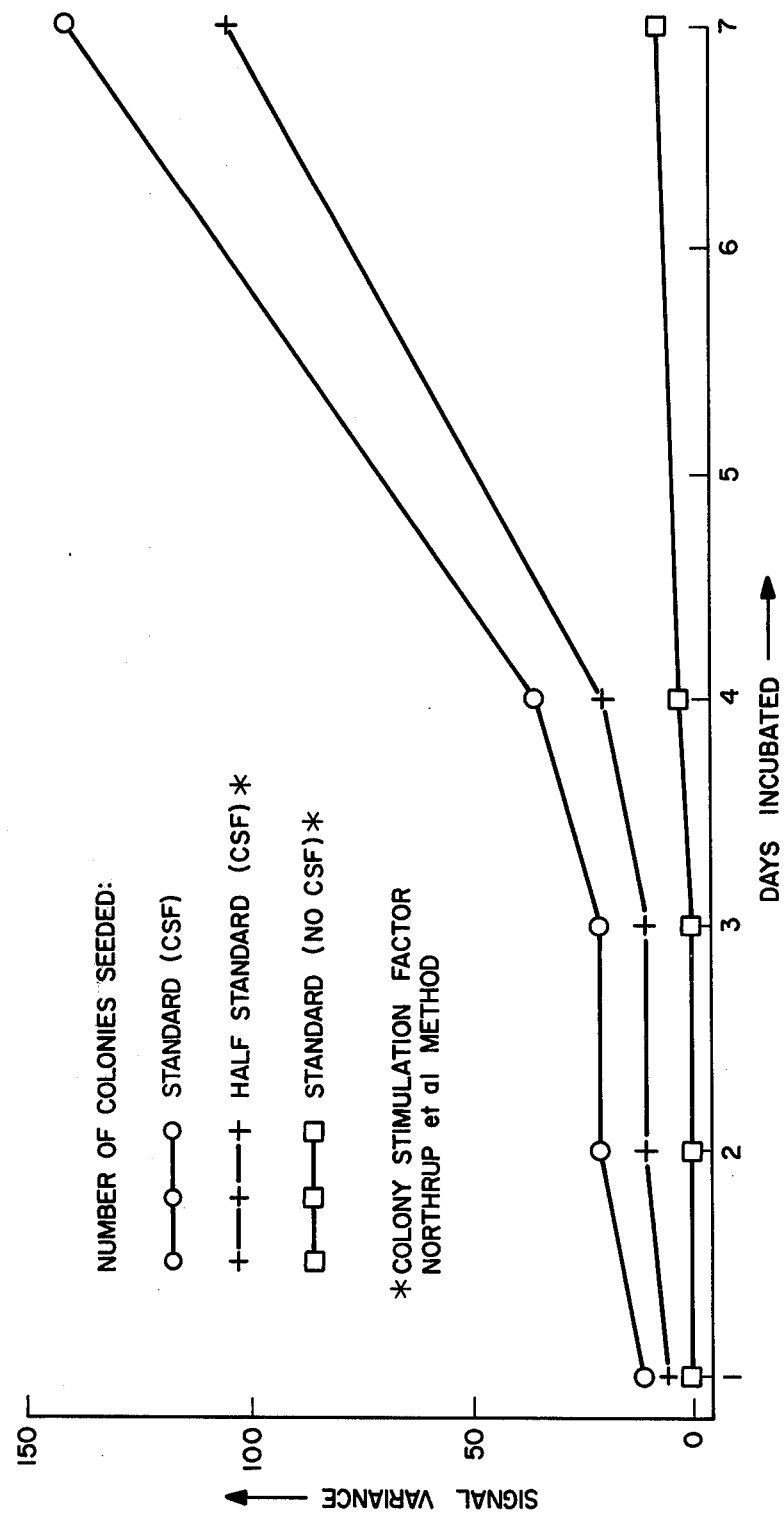
FIG. 4 is a graphical representation of typical measurements of bone marrow granulocyte precursor colonies as to dilutions, with and without J. D. stimulative factor (CSF) according to the method described by J.D. Northrup, et al. in the "Journal of the National Cancer Institute" 48,629 (1972).

In an embodiment for counting bone marrow granulocyte precursor colonies in a three dimensional gel medium, a 2 inch diameter circular reticle was made by photo-reducing a computer generated pattern consisting of 500 alternately clear and opaque segments onto a glass photographic plate. The gel medium causes the colonies to retain their relative positions throughout the test period, which may be a week or more. However, this is not necessary for successful operation. Test tubes containing growing bone marrow aspirates (sample 10) were imaged by camera lens 16 at unity magnification on reticle 18 as it rotated. The signal from detector 20, a photomultiplier tube, was synchronously detected by means of a Princeton Applied Research lock-in amplifier with reference signal 24 from optical pick-off 26 on the edge of the reticle. The low-audio, analog amplifier signal was digitized by means of a digital voltmeter and the variance of the signal computed. In order to examine a representative volume of the test tube, the tube was slowly rotated by drive 14 during measurement. Synchronous detection was employed to minimize the effects of reticle flutter. The results of a typical series of measurements are given in FIG. 4.

Figure 2:
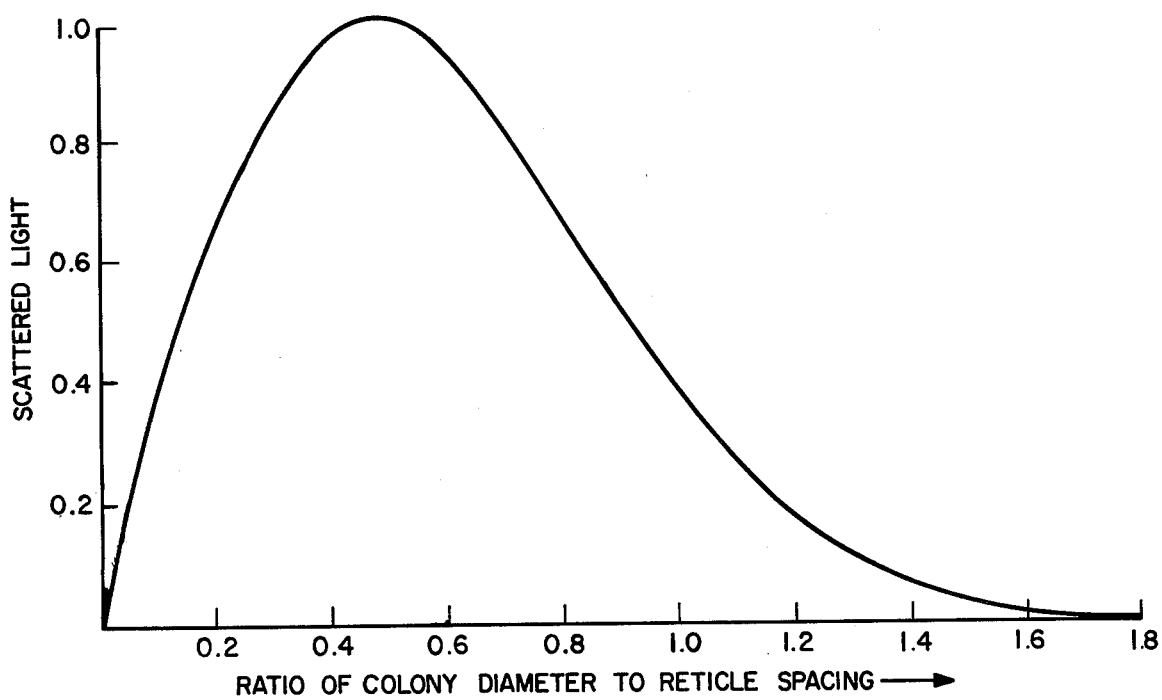
FIG. 2 is a graphical representation of the relative signal amplitude produced by Gaussian shaped objects of uniform integrated intensity but differing in size, showing the effect of spacing in the reticle pattern of the size of the objects that are counted.

It is significant that, with the rotating reticle instrument, colony growth or non-growth as revealed by the signal variance, is evident within 3 days after innoculation of the medium. A trained observer cannot make this determination in less than a week after innoculation by prior techniques. The counter using spatial frequency information tends to ignore background haze, fingerprints, bubbles, and striations, etc. FIG. 2 graphically shows the effect of selecting the spacings in the reticle pattern on the size of the colonies that will be detected. Note that the peak amplitude output occurs when the diameter of the colonies is approximately the same size as one-half the reticle spacing. That means, that when the size of the objects-of-interest is known, a reticle having the proper spacing, i.e., one having opaque and transmissive sections wherein the width of each section is approximately twice the diameter of the object to be measured, may be chosen to specifically measure objects of that size. The present invention is intended to specifically include all known reticle patterns that can provide the modulation required.

Figure 3:
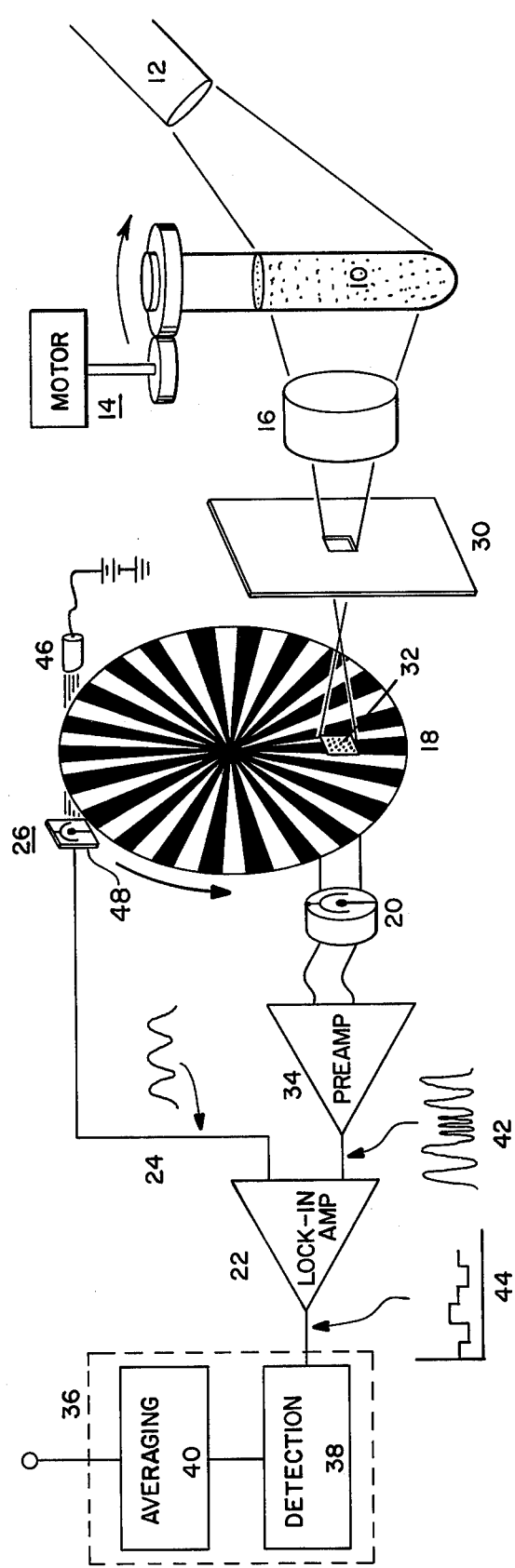
FIG. 3 is an illustrative depiction, partially in schematic form, of an arrangment of an embodiment of the present invention for counting bone marrow granulocyte precursor colonies in a three-dimensional gel medium.

FIG. 3 is a depiction of an embodiment of the present invention for measuring the number of objects that are present in the system's field of view, such as the number of objects-of-interest in sample 10. The sample is illuminated by light source 12 which may be any suitable light source such as the illumination source often employed for microscopic studies, and is rotatably driven by drive 14 for the purpose of obtaining a more complete and accurate interrogation of the sample. Optics 16 converge and convey the light that has been conveyed from sample 10 through aperture plate 30, and focus it on reticle 18 at aperture image 32. Aperture plate 30 is included as a light screen to prevent extraneous light from appearing on the reticle and restricts the view seen by optics 16 to an area within the edges of the sample. If the sample is held within a vessel such as a test tube, aperture plate 30 is employed, at least in part, to block-out reflections from the edges of the rotating tube, which reflections would otherwise cause erroneous counts. Reticle 18 is rotatably driven to present alternating sections of opaque and transmissive portions under aperture image 32, and thereby continuously modulate the every changing image of sample 10. Photodector 20, which may be a photomultiplier tube or photo-diode, or the like, is in alignment with image 32 to detect the modulated image of sample 10, and convert the image into an electric signal. The signal may be coupled to detector preamplifier 34 to increase signal level. Output 42 of preamplifier 34 includes information definitive of the square root of the number of objects present in the field-of-view, plus extraneously and electronically generated noise and modulations that are unrelated to the information-of-interest. Therefore, output 42 of preamplifier 34 is coupled to lock-in amplifier 22 which is a synchronous detector that is sensitive only to signals that are at or near the frequency of output 24 of pick-off 26. That is, output 42 is compared to output 24 in lock-in amplifier 22 to clean-up the signal by retaining only those portions of output 42 that are at or near the frequency of output 24.

Control output 24 is provided by pick-off 26. Pick-off 26 may be photodetector 48 in alignment with, and opposite reticle 18 from, light source 46. The output of photodetector 48 is a signal that is modulated only by the reticle pattern of reticle 18. Thereby, since the system is interested only in the modulation of the image of sample 10 by reticle 18, comparison of output 42 with output 24 in lock-in amplifier 22 eliminates all signal portions that are not related to the imposed modulation of reticle 18. Pick-off 26 and image 32 must each be at transmissive sections of reticle 18 at the same time to provide synchronous detection.

Output 44 of lock-in amplifier 22 is definitive of the number of objects of interest in the system's-field-of-view. Output 44 is a rectified sine wave that has been passed through a low-pass filter to provide a noiseless d.c. level that will most likely vary as the sample is rotated. Output 44 is coupled through presentation means 36 to provide the output in the form desirable. Means 36 may include detection circuitry 38 for further reducing the possibility of false counts, if detection has not already been accomplished in amplifier 22, and averaging circuitry 40 for averaging the count taken over a selected period. Averaging circuitry 40 may be an integrator that will accumulate the count for some period of time, such as 30 seconds. Either output 44 or the output of presentation means 36 may be converted into a direct digital readout with known and readily available devices.

The present invention is therefore an improvement over counting techniques in many technologies wherein, for the most part, counting has been conducted visually by trained observers. The advantages of the present invention are particularly evident where relative counts are important, such as when the number of objects in a given sample is increasing or decreasing over a period of time and the degree of change is significant. Such a situation is the example described above for counting bone marrow granulocyte precursor colonies. Examples wherein the present invention also provides significant advantages over prior techniques is in the determination of size distribution in powders, particulate matter in gases, events represented by grains in nuclear emulsions, cloud cover in satellite photographs, and bacterial colonies in cultures.

To those skilled in the art it will be obvious upon a study of this disclosure that the present invention permits a variety of modifications in structure and arrangement and hence can be given embodiments other than those particularly illustrated and described herein, without departing from the essential features of the invention within the scope of the claims annexed hereto.

What is claimed is:

1. A system for counting the number of objects in a selected sample by automatic measurement of spatial frequency components in the system's field-of-view comprising;
    a sample of interest that includes therein an undetermined number of objects to be counted by the system;
    means for interrogating said sample and providing an electrical output responsive to the spatial frequency components in said field of view wherein said spatial frequency components are definitive of said number of objects;
    said interrogating means including a light source for illuminating said sample;
    a movable reticle means having alternating opaque and transmissive portions positioned in the optical path between said light source and said photodetector means;
    drive means coupled to said movable reticle to cause said alternate opaque and transmissive portions to pass between said light source and photodetector means at a predetermined frequency;
    the width of said alternate opaque and transmissive portions on said reticle being chosen to provide a predetermined ratio of object size to the width of said alternating opaque and transmissive portions.

2. The system as set forth in claim 1 wherein;
    said ratio is optimized when the width of each opaque and transmissive portion is approximately twice the diameter of the object to be measured.

3. The system of claim 1 wherein said interrogating means further includes means for synchronously detecting the output of said photodetector at the rate of said modulation.

4. The system of claim 3 wherein said reticle is driven such that the movement of the pattern of said reticle is orthogonal to said optical path.

5. The system of claim 4 wherein said interrogating means further includes optical means for focusing said illumination onto said reticle and said reticle is optically a square wave device in that it has light transmissive portions and opaque portions.

6. The system of claim 5 wherein said interrogating means further includes means for holding and rotating said sample to permit continuous interrogation of said sample about its perimeter.

7. The system of claim 6 wherein said synchronously detecting means includes an optical pick-off near the perimeter of said reticle for providing a varying electrical signal responsive only to the modulation generated by said reticle, and a lock-in amplifier coupled to both the output of said photodetector and said pick-off for providing an output that is responsive only to the number of objects counted.

8. The system of claim 7 wherein said lock-in amplifier includes a low-pass filter for providing a d.c. output as the output of said lock-in amplifier.

9. The system of claim 8 wherein said holding and rotating means includes a test tube for holding said sample, and a rotatably driven test tube holder.

10. The system of claim 9 wherein said system is a bone marrow granulocyte precursor colony counter, said sample-of-interest is a bone marrow sample of stem colonies, and the output of said interrogating means is equal to the square root of the number of objects counted.

11. The system of claim 1 wherein;
    said reticle is a wheel having a radiating spoke pattern of alternating transmissive and opaque sections.

* * * * *